US008823923B2

(12) United States Patent
Berman et al.

(10) Patent No.: US 8,823,923 B2
(45) Date of Patent: Sep. 2, 2014

(54) TRIPLE ISOTOPE METHOD AND ANALYZER FOR TOTAL ENERGY EXPENDITURE MEASUREMENTS

(75) Inventors: Elena S. F. Berman, Mountain View, CA (US); John R. Speakman, Stonehaven (GB); Manish Gupta, Mountain View, CA (US); Edward L. Melanson, Jr., Denver, CO (US); Susan L. Fortson, Mountain View, CA (US); Douglas S. Baer, Menlo Park, CA (US)

(73) Assignee: ABB Research Ltd., Zurich (CH)

( * ) Notice: Subject to any disclaimer, the term of this patent is extended or adjusted under 35 U.S.C. 154(b) by 0 days.

(21) Appl. No.: 13/426,220

(22) Filed: Mar. 21, 2012

(65) Prior Publication Data

US 2013/0027705 A1    Jan. 31, 2013

Related U.S. Application Data

(60) Provisional application No. 61/511,652, filed on Jul. 26, 2011.

(51) Int. Cl.
*G01N 33/48* (2006.01)
*G01N 21/03* (2006.01)
*G01N 21/35* (2014.01)
*G01N 21/39* (2006.01)

(52) U.S. Cl.
CPC .......... *G01N 21/031* (2013.01); *G01N 21/3577* (2013.01); *G01N 21/39* (2013.01)
USPC ........................................................... 356/39

(58) Field of Classification Search
USPC .................................. 356/3; 435/29; 703/11
See application file for complete search history.

(56) References Cited

U.S. PATENT DOCUMENTS

| 6,795,190 | B1 | 9/2004 | Paul et al. | |
| 6,839,140 | B1 | 1/2005 | O'Keefe et al. | |
| 7,468,797 | B1 * | 12/2008 | O'Keefe et al. | 356/437 |
| 2006/0020440 | A1 * | 1/2006 | Hellerstein | 703/11 |
| 2009/0305322 | A1 * | 12/2009 | Hegg et al. | 435/29 |

OTHER PUBLICATIONS

Kerstel et al., "Laser Spectrometry Applied to the Simultaneous Determination of the . . . Isotope Abundances in Water", IAEA-TECDOC-1247 (2001), Proceedings of an Advisory Group meeting held in Vienna, Sep. 20-23, 1999; pp. 7-13.

(Continued)

*Primary Examiner* — Tarifur Chowdhury
*Assistant Examiner* — Jamil Ahmed
(74) *Attorney, Agent, or Firm* — Thomas Schneck; Mark Protsik

(57) ABSTRACT

A method of measuring energy expenditure in a living subject comprises: (a) administering a specified dose of doubly-labeled water ($^2H_2{}^{18}O$) to a living subject; (b) obtaining samples at three or more times of body water from the living subject; (c) measuring $^2H/^1H$, $^{17}O/^{16}O$ and $^{18}O/^{16}O$ ratios in each of the obtained samples using optical spectroscopy; and (d) determining (1) a combined value of flux of body water and exhaled carbon dioxide from a change in measured $^{18}O/^{16}O$ over time, (2) a value of flux of body water alone from a change in measured $^2H/^1H$ over time, and (3) a reference value of isotopic background fluctuation from a change in measured $^{17}O/^{16}O$ over time. Using $^{17}O$ measurements to estimate background fluctuations of the $^2H$ and $^{18}O$ decreases the required isotope dosing of subjects or decreases uncertainty at current dosing levels.

9 Claims, 3 Drawing Sheets

(56) References Cited

OTHER PUBLICATIONS

Lis et al., "High-Precision Laser Spectroscopy D/H and . . . Measurements of Microliter Natural Water Samples", Analytical Chemistry, vol. 80, No. 1, Jan. 1, 2008; pp. 287-293.

Speakman et al., "Revised equations for calculating $CO_2$ production from doubly labeled water in humans", The American Physiological Society, Copyright 1993; pp. E912-E917.

Speakman, "The history and theory of the doubly labeled water technique", American Society for Clinical Nutrition 1998;68; pp. 932S-938S.

Schoeller, "Measurement of Energy Expenditure in Free-Living Humans by Using Doubly Labeled Water", American Institute of Nutrition 1988; pp. 1278-1289.

Weir, "New Methods for Calculating Metabolic Rate with Special Reference to Protein Metabolism", J. Physiol. (1949) 109, pp. 1-8.

\* cited by examiner

TRIPLE ISOTOPE METHOD AND ANALYZER FOR TOTAL ENERGY EXPENDITURE MEASUREMENTS

CROSS-REFERENCE TO RELATED APPLICATION

The present application claims priority under 35 U.S.C. 119(e) from U.S. provisional patent application 61/511,652, filed Jul. 26, 2011.

TECHNICAL FIELD

The present invention relates to isotopic analysis of water samples and instruments therefor. The invention also relates to diagnostic methods for measuring total energy expenditure in living subjects using such isotopic analysis of water.

BACKGROUND ART

The high prevalence of obesity in the US is a major public health concern, as overweight and obese individuals are at increased risk for many chronic diseases. Obesity stems from an imbalance between total caloric consumption and total energy expenditure (TEE), although the causes of this imbalance remain debated. Accurate measurements of TEE therefore play a pivotal role in understanding and ultimately reversing this epidemic.

TEE can be measured using direct (measurement of heat production) or indirect (measurement of respiratory gas exchange) calorimetry, but neither of these approaches are practical for measuring TEE in free living subjects. The gold standard for measuring TEE in free-living individuals is the doubly labeled water (DLW) method, which is based on the principle that the oxygen in body water is in complete isotopic equilibrium with the oxygen in dissolved respiratory carbon dioxide due to the action of carbonic anhydrase. The consequence of this exchange is that an isotopic label of oxygen introduced into body water is eliminated by the combined flux of body water and the exhaled carbon dioxide. Lifson and colleagues reasoned that, since hydrogen is found only in water and not in carbon dioxide, the elimination of a hydrogen isotope would be affected solely by the flux of body water. Thus the difference in the rates of isotope elimination of simultaneously administered oxygen and hydrogen labels is a measure of $CO_2$ production. Review of the doubly labeled water technique, validation of its assumptions, and equations for calculating metabolic $CO_2$ production from the isotopic measurements may be found, e.g., in D. A. Schoeller, "Measurement of Energy Expenditure in Free-Living Humans by Using Doubly Labeled Water", Journal of Nutrition 118, pages 1278-89 (1988); J. R. Speakman, S. Nair, and M. I. Goran, "Revised equations for calculating CO2 production from doubly labeled water in humans", American Journal of Physiology 264, pages E912-7 (1993); J. R. Speakman, "The history and theory of the doubly labeled water technique", American Journal of Clinical Nutrition 68(suppl), pages 932S-938S (1998); and others, including references cited in the aforementioned papers.

Despite its usefulness, the DLW, method has some limitations. First, the test is expensive to perform due to the need for large quantities of $H_2^{18}O$ (approx. 0.25 gram per kilogram of a subject's fat-free mass) in addition to $^2H_2O$. This expense is predominantly due to the cost of the $^{18}O$ that is used to label subjects. High levels of $^{18}O$ are required to distinguish the dose from fluctuating background isotope levels after 14-28 days of elimination; it currently costs $300-$400 for the $^{18}O$ required to perform a DLW measurement on an adult subject (50-100 kg fat-free mass). Thus, widespread adoption of the DLW method has been limited by its high cost.

High levels of $^{18}O$ tracer are needed to ensure that unknown fluctuations in the background isotope levels over time do not contribute excessively to measurement uncertainty. While the isotopic composition of atmospheric oxygen ($O_2$) is itself essentially constant within the time frame of TEE testing, living test subjects also require regular food and water intake for good health, both of which are background sources of hydrogen and oxygen intakes. The isotopic composition of both natural water and various water-bearing foodstuffs vary according to factors such as local evaporation and precipitation rates at their source. Accordingly, daily variations in dietary and beverage intake by the test subjects contribute to the uncertainty in background isotope levels. This uncertainty in the background levels increases the isotope dose that must be administered and contributes to the uncertainty in the DLW measurements as compared to the reference calorimetry measurements of TEE in validation studies. Individual measurements are only precise to ±5%, so the method is currently most suitable for studies of groups rather than individual variation.

The proposed invention aims to address these two problems by significantly reducing the cost of the DLW method and improving the individual accuracy of the measurements.

E. R. T. Kerstel, R. Van Trigt, N. Dam, J. Reuss, H. A. J. Meijer, "Laser spectrometry applied to the simultaneous determination of the $\delta^2H$, $\delta^{17}O$, and $\delta^{18}O$ isotope abundances in water", IAEA-TECDOC-1247, pp. 7-13 (2001) describes application of infrared laser spectrometry to the simultaneous determination of the relative $^2H/^1H$, $^{17}O/^{16}O$, and $^{18}O/^{16}O$ isotope abundances in natural water. The method uses a narrow line width color center laser directed into gas cells equipped with multiple-pass reflection optics (for ≈20 m path length) to record the direct absorption spectrum of low-pressure gas-phase water samples in the 3 μm spectral region (ro-vibrational transitions around 3663 cm$^{-1}$). The precision of the technique is shown to be 0.7‰ for $\delta^2H$ and 0.5‰ for $\delta^{17}O$ and $\delta^{18}O$, while the calibrated accuracy is about 3‰ and 1‰, respectively.

G. Lis, L. I. Wassenaar, and M. J. Hendry, "High-Precision Laser Spectroscopy D/H and 18O/16O Measurements of Microliter Natural Water Samples", Anal. Chem. 80(1), pp. 287-293 (Jan. 1, 2008) describes use of off-axis integrated cavity output spectroscopy (OA-ICOS) for isotopic analysis ($\delta D$ and $\delta^{18}O$) of water samples. A liquid autosampler injects from 0.2 to 1.0 μL of $H_2O$ into a pre-evacuated optical cavity via heated (70° C.) injection port to facilitate complete evaporation and vapor transfer through a tube. The highly reflective mirrors of the optical cavity extend the average optical path length to ~3000 m allowing the use of infrared diode lasers operated at room temperature. The laser wavelength is tuned over the absorption spectrum of the isotopologues of interest of the injected $H_2O$ sample. Random instrumental drift was corrected by systematically spacing standard injections within the autorun and conducting linear interpolations. Potential intersample memory effects and mixing of water samples were overcome by using five sequential injections of each sample, discarding the first two injection results and accepting the mean of the final three injection results. Measurement accuracies of ±0.8‰ for $\delta D$ and ±0.1‰ for $\delta^{18}O$ were achieved.

SUMMARY DISCLOSURE

The innovation involves measuring the changes over the sampling time in the background isotope levels of $^{18}O$ and $^2H$ indirectly by measuring the undosed $^{17}O$ stable isotope of oxygen in the respective body water samples. Natural factors (e.g. fractionation) affect isotopes similarly leading to a correlation in the abundances of different isotope species, such as that found in the meteoric water line. Previous studies have shown in body water measurements that background fluctuations in $^{2}H$ and $^{18}O$ are correlated with an average R value of 0.79. Assuming a similar correlation with $^{17}O$, using $^{17}O$ measurements to estimate the background fluctuations of the $^{2}H$ and $^{18}O$ will allow researchers to substantially decrease the required isotope, reducing the cost of the $^{18}O$ label to an estimated $60-$80, and thus addressing the first major problem with the DLW technique. Alternatively the dose could be maintained at its current level, and the $^{17}O$ measurement would provide an estimated five-fold decrease in the uncertainty of the method due to background fluctuation (addressing the second major problem with the method detailed above).

Measurement of the $^{17}O$ isotope by conventional Isotope Ratio Mass Spectrometry (IRMS) with adequate precision to measure the background correlation is sufficiently expensive (e.g. $500-$1000 per sample) to obviate the potential price gains available by measuring the background fluctuations. However, recently developed optical spectroscopy instruments (e.g. using off-axis integrated cavity output spectroscopy, Off-Axis ICOS) can simultaneously and inexpensively (<$50 per sample) measure $^{2}H$, $^{18}O$, and $^{17}O$ in liquid water samples.

DETAILED DESCRIPTION

We have demonstrated the technical feasibility of utilizing optical spectrometry for DLW measurements ($^{2}H/^{1}H$ and $^{18}O/^{16}O$) of TEE. The test results prove that these instruments are capable of analyzing samples for standard TEE measurements with accuracy comparable to (or exceeding that) obtained with a conventional IRMS. We have additionally demonstrated the use of optical spectrometry to precisely measure $^{17}O/^{16}O$. Furthermore, preliminary IRMS studies have shown that enrichment of $^{18}O$ does not result in a concurrent enrichment of $^{17}O$, opening up the possibility of using the $^{17}O/^{16}O$ isotope ratio to measure the isotopic background fluctuations during DLW experiments.

The ratios $^{2}H/^{1}H$, $^{17}O/^{16}O$ and $^{18}O/^{16}O$ are conventionally described relative to Vienna Standard Mean Ocean Water (VSMOW), available as NIST RM 8535a, which has $^{2}H/^{1}H$ of 155.76±0.05 ppm, $^{17}O/^{16}O$ of 379.9±0.8 ppm, and $^{18}O/^{16}O$ of 2005.20±0.45 ppm. The observed natural range of $^{2}H/^{1}H$ is from −836‰ to +180‰ (0.0000255 to 0.0001838 molar fractions of $^{2}H$) for all forms of hydrogen (including from natural gas and atmospheric hydrogen) and from −495‰ to +129‰ for natural water originating as precipitation. The observed natural range of $^{18}O/^{16}O$ is from −62.8‰ to +109‰ (0.001875 to 0.002218 molar fractions of $^{18}O$) for all forms of oxygen (including that found in marine carbonates, atmospheric nitrogen oxides, etc.) and from −62.8‰ to +31.3‰ for natural water originating as precipitation. In natural waters, $\delta^{17}O$ variation relative to VSMOW has been found to be 0.5281±0.0015 times the variation in $\delta^{18}O$. [T. B. Coplen et al, Isotope-Abundance Variations of Selected Elements, Pure Appl. Chem., Vol. 74, No. 10, pp. 1987-2017, 2002] For purposes of the present invention, the measured values of $\delta^{2}H$, $\delta^{17}O$ and $\delta^{18}O$ are likewise described relative to the VSMOW standard, using any of a variety of reference samples of known isotopic composition to calibrate the measurements from the OA-ICOS instrumentation. Measured $\delta^{17}O$ is used to adjust for the effect of isotopic background fluctuations upon the isotope elimination rate from the body water.

Figure 1:
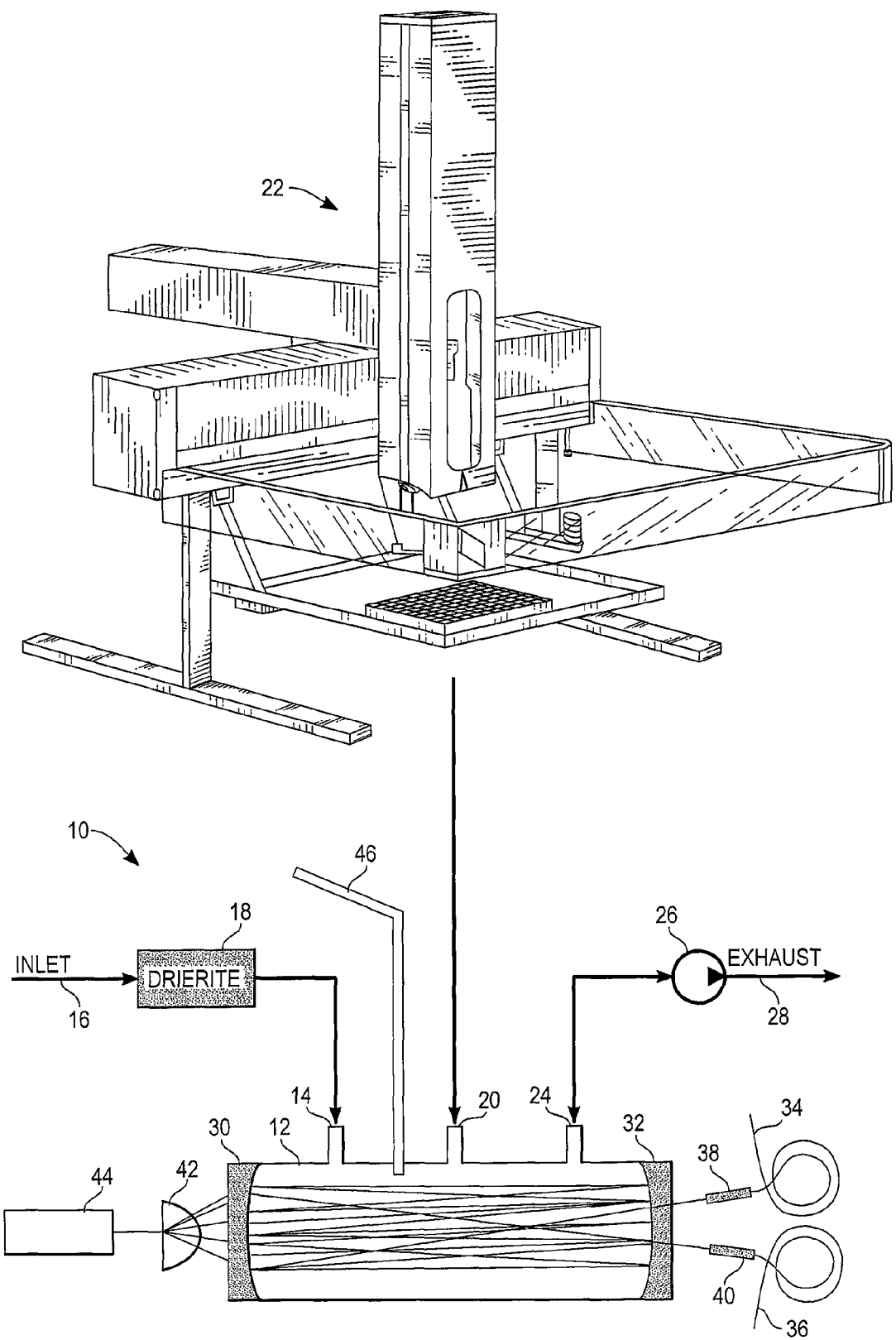
FIG. 1 shows a schematic plan view of an isotopic water analyzer for use with a doubly-labeled water experiment in accord with the present invention.

With reference to FIG. 1, an isotopic water analyzer uses off-axis integrated cavity output spectroscopy (OA-ICOS) to obtain fully resolved absorption spectra containing all of water's major isotopologues ($H_2O$, $H^2HO$, $H_2^{17}O$ and $H_2^{18}O$) simultaneously. Isotopic water analyzers are available that can measure liquid water samples (as described, e.g., in U.S. Pat. No. 6,839,140 to O'Keefe et al.) as well as water vapor samples. Los Gatos Research, Inc. of Mountain View, Calif. (the assignee of the present invention) supplies isotopic water analyzers (e.g. model 911-0034) that performs water vapor measurements, as well as other analyzers (e.g. model IWA-45EP) that can perform both water vapor and liquid water measurements.

OA-ICOS instruments and their operation are described in U.S. Pat. No. 6,795,190 to Paul et al., as well as in U.S. Pat. No. 7,468,797 to O'Keefe et al. Off-axis light injection into the optical cavity provides spatial separation of reflections from the cavity mirrors that extend the effective optical path length to ~3000 m, resulting in increased absorption and allowing the use of economical, room-temperature, infrared diode lasers. The laser wavelength from one or more laser sources is tuned over a selected absorption spectrum band of water capable of distinguishing between the various major isotopologues of water, such as in the vicinity of 1350 to 1400 nm, and the resulting absorption is measured to high resolution.

Thus, as seen in FIG. 1, an isotopic water analyzer 10 includes a sample cell 12 having a set of access ports 14, 20 and 24. The access port 14 is an inlet for dry air. Room air can enter from an intake 16, flow through a drierite dryer 18 and then pass through the access port 14 into the sample cell 12. The dry air flow serves to help remove any residual water from a previous sample by means of flushing and dilution. The access port 20 is a water sample inlet coupled to an autoloader 22 to receive injections of a water sample to be measured. A typical sample volume is approximately 1 μL of liquid water per injection. The third access port 24 is an outlet coupled through a diaphragm pump 26 to an exhaust 28.

The sample cell 12 has two highly reflective mirrors 30 and 32 at opposite ends, which define an optical cavity. In the depicted embodiment, two laser sources 34 and 36 direct laser beams through respective collimation lenses 38 and 40 and through one of the mirrors 32 into the optical cavity. In this embodiment, two lasers of slightly different wavelength bands are used to extend the available wavelengths to a full absorption spectrum of all of the major water isotopomers. The lasers can be tunable diode lasers or diode-pumped tunable fiber lasers, for example, and may have respective infrared wavelengths centered near 1365 nm and 1390 nm, respectively. Since the laser beams do not need to be resonantly coupled into the sample cell (i.e. precise beam alignment is not critical), the analyzer is inherently robust thermally and mechanically. The long effective path length of the light inserted into the cavity means that a far wider range of absorbance values (optical depth) can be recorded.

Light exiting the optical cavity, such as through one of the mirrors 30 of the sample cell 12, is collected by a lens 42 and detected by an optical detector 44 responsive to the laser wavelengths, such as an InGaAs detector. The analyzer may operate in a ringdown mode, wherein pulses of laser light are injected and the intensity decay time corresponds to the absorbance of the sample at that particular laser wavelength. The pulses may sweep through the absorption spectrum of the water sample and the data analyzed to determine peaks of absorbance for each of the isotopomers of water.

A temperature probe 46 may be provided to measure sample cell temperature and thermal control may be used for ultra-stable measurement with essentially no drift.

Figure 2A:
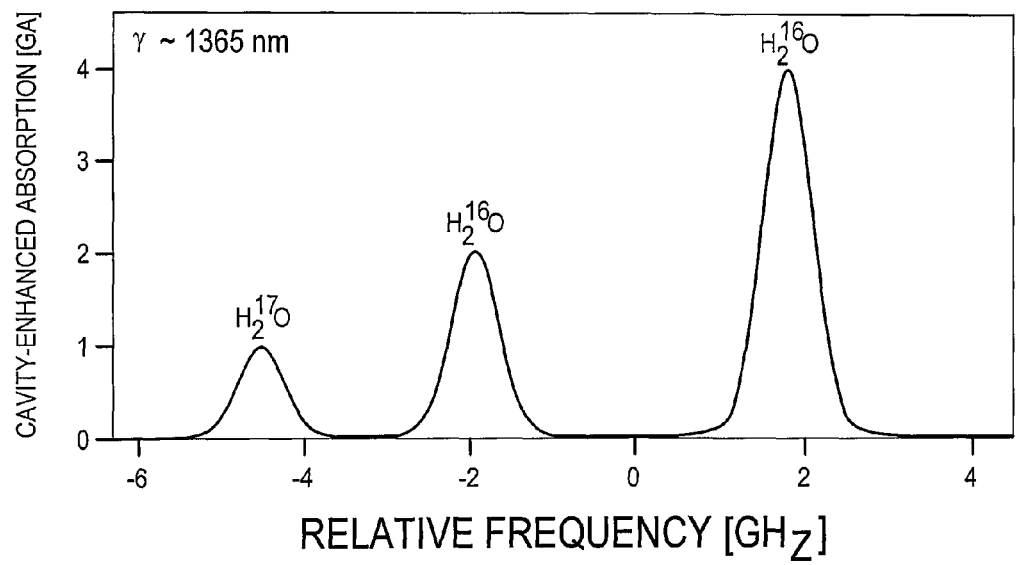
FIGS. 2A and 2B shows graphs of absorption spectrum of water isotopomers near 1365 and 1390 nm, respectively, allowing precise measurements of the $^{17}O/^{16}O$, $^{18}O/^{16}O$, and $^{2}H/^{1}H$ isotope ratios.

Demonstration of Precise Optical Measurements of the $^{17}O/^{16}O$ Isotopic Ratio We have fabricated an instrument which measures $^{17}O$, $^{16}O$ and the $^{17}O/^{16}O$ isotopic ratio using optical spectroscopy. FIG. 2A shows the optical absorption spectrum in a region in the near-infrared near 1365 nm. Possible wavelength regions for the $^{17}O$ measurements include those near 1365 nm (seen in the Figure), near 1390 nm and near 1400 nm, as well as numerous others (such as near 2730 nm for the Kerstel et al. paper described above) provided a suitable laser source is available.

Figure 2B:
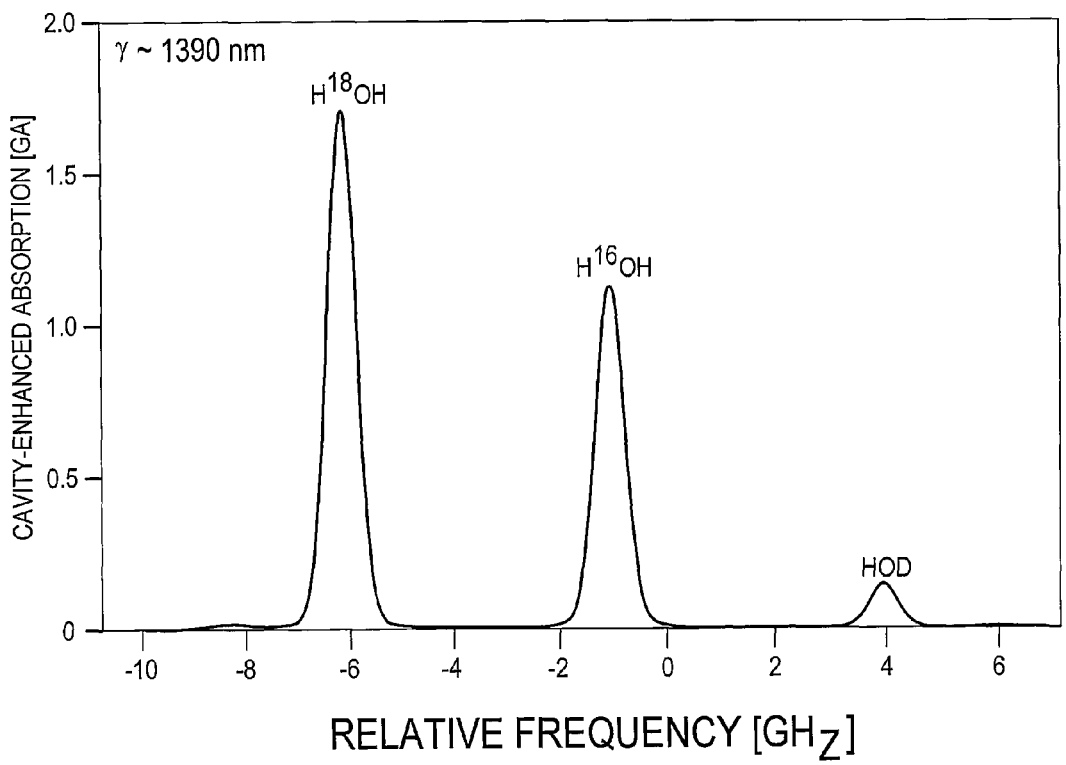

We have also fabricated instruments which measure $^{18}O$, $^{16}O$, $^2H$, $^1H$, and the $^{18}O/^{16}O$ and $^2H/^1H$ isotopic ratios using optical spectroscopy. FIG. 2B shows the optical absorption spectrum in a region in the near-infrared near 1390 nm. While there are dozens of other possible absorption regions, this particular one is well characterized for $^{18}O$ and $^2H$ measurements.

A single instrument as in FIG. 1 may combine capabilities to obtain both of the absorption spectra in FIGS. 2A and 2B. Alternatively, the spectra in FIGS. 2A and 2B and corresponding measurements of their respective isotopic ratios can be obtained using two separate instruments. The relative quantities of each isotope in a sample can be determined directly from the relative absorption peaks for each major isotopomer of water. While this embodiment uses absorption of infrared light by the water in the 1350-1400 nm range, water's many other absorption bands could also be used, provided the various isotopomers can be readily distinguished.

Figure 3:
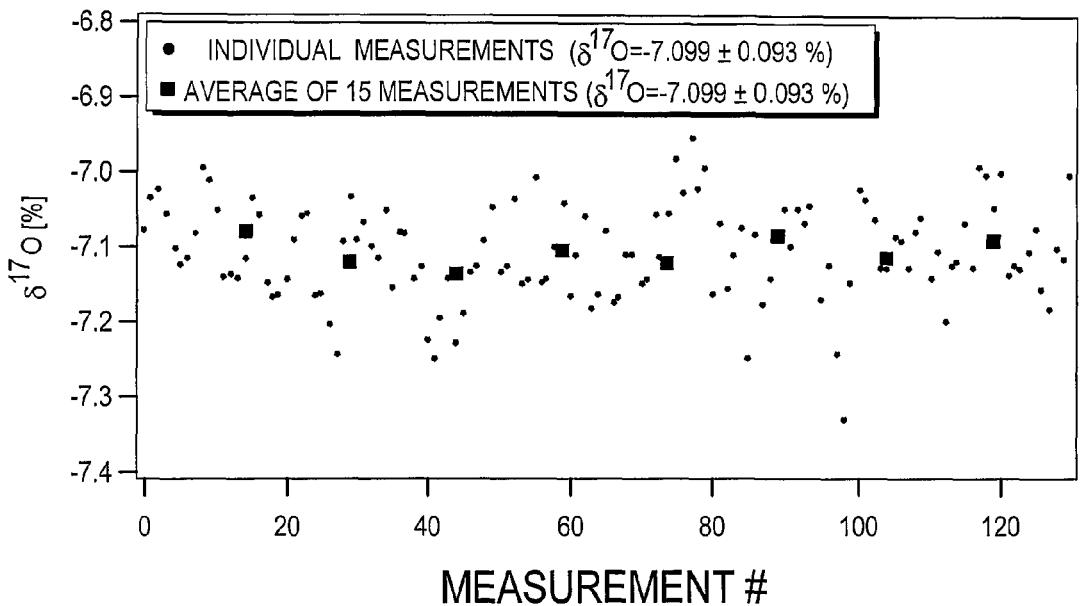
FIG. 3 shows a graph of repeated measurements of $\delta^{17}O$ for a single water sample against internal standards.

FIG. 3 demonstrates the preliminary measurement precision which we are able to achieve with this instrument, ±0.093‰ in $\delta^{17}O$ at 150 samples a day averaging down, to ±0.026‰ at 10 samples per day. Further improvements in the precision are underway and are expected to improve the precision to better than ±0.010‰.

Demonstration that $^{18}O$ Enrichment does not Result in $^{17}O$ Enrichment

Figure 4:
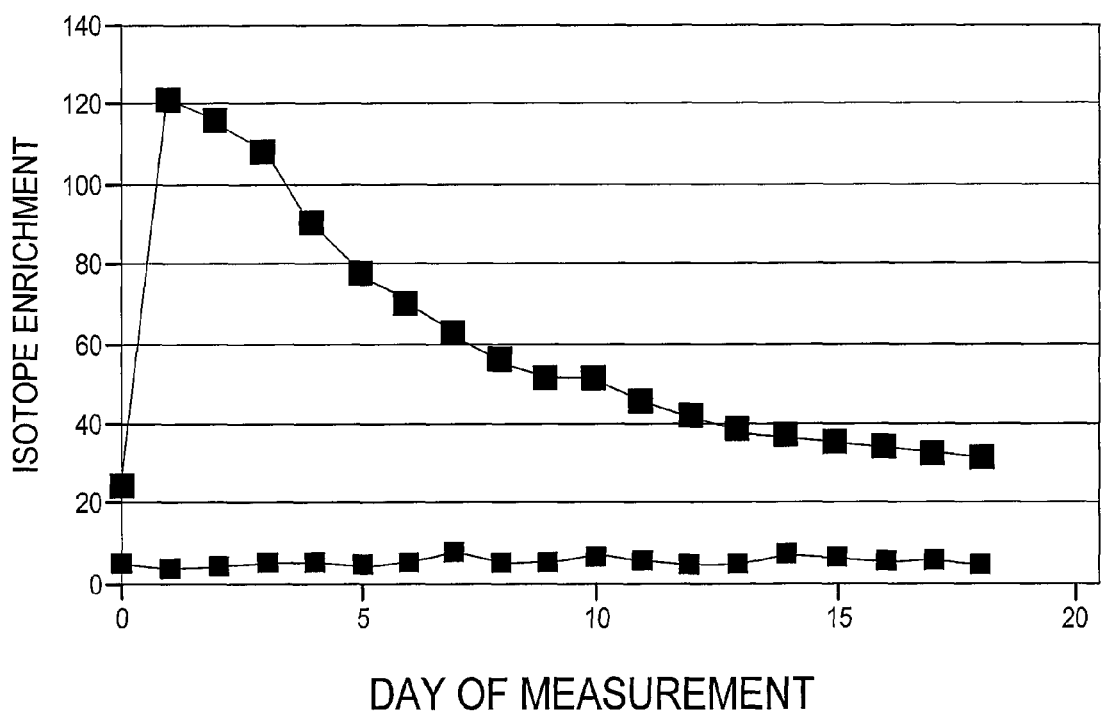
FIG. 4 shows a graph of enrichments measured by IRMS over time of $^{18}O$ and $^{17}O$ following a bolus dose administration in a human subject (Adolescent in Kenya—hence high background level of $^{18}O$). There is no discernible elevation of the $^{17}O$ enrichment coincident with the rise in $^{18}O$.

The industrial process by which $^{18}O$ is enriched depends on physical fractionation which may inadvertently also enrich $^{17}O$. Estimates of the levels of $^{17}O$ in dose solutions suggest that it is only enriched to about $\frac{1}{300}^{th}$ the level of $^{18}O$. Consequently, if subjects were dosed with $^{18}O$ to a level of 100 ppm above background, the enrichment in $^{17}O$ would be only 0.3 ppm. In a pilot study we have measured $^{17}O$ levels using IRMS in 19 subjects involved in a DLW protocol where urine samples were collected daily. FIG. 4 shows that there is no detectable effect of the dose water on background $^{17}O$ levels. This observation is critical in utilizing $^{17}O$ to correct for naturally occurring background isotopic fluctuations in $^{18}O$ and $^2H$.

Hence, after measuring $^{17}O/^{16}O$ and $^{18}O/^{16}O$, the measured change in $^{18}O/^{16}O$ can be proportionally adjusted by dividing its value by the corresponding change in $^{17}O/^{16}O$. That is, measured changes in $\delta^{17}O$ are entirely due to background enrichment levels and can serve as a proxy for otherwise unknown background fluctuations in $\delta^{18}O$. It is also assumed that measured changes in $\delta^{17}O$ can also serve as a proxy for background fluctuations in $\delta^2H$, whereby the measured change in $^2H/^1H$ is likewise proportionally adjusted by division with the corresponding change in $^{17}O/^{16}O$.

Testing Protocol

The innovation involves no change in current DLW protocols other than the permitted change in isotope dose and subsequent analysis of $^{17}O$ in addition to $^2H$ and $^{18}O$. Any DLW protocol can be used with the innovation. In general, the DLW technique involves introducing stable isotopes of both oxygen ($^{18}O$) and hydrogen ($^2H$) into a human or animal subject, often but not exclusively by oral administration of labeled water. The subsequent enrichment of the body water is then measured over time to ascertain the differential rates of elimination of the $^{18}O$ and $^2H$. Body water can be measured from blood, plasma, urine, saliva, and/or exhaled breath. The difference in the elimination rates of the $^{18}O$ and $^2H$ can then be used to calculate the total energy expenditure (TEE) of the free-living subject. The innovation involves measuring the $^{17}O$ in the body water samples and using this measurement to improve the calculations of TEE. Specific examples of TEE testing protocols utilizing the innovation ($^{17}O$ measurements) to either reduce the uncertainty in the calculations or to reduce the cost of the test are provided below. Also included below is a specific example of how to analyze the sample using the preferred instrument to measure the isotopes.

Example Testing Protocol for Reduced Uncertainty

TEE is measured for a 14 day period using DLW. Upon subject arrival for the study, body weight is measured to ±0.1 kg and a baseline urine sample is obtained for determination of background enrichments of $^2H$, $^{18}O$ and $^{17}O$. Subjects are then given an oral dose of 0.23 g $H_2^{18}O$ and 0.12 g $^2H_2O$ per kg of total body water (estimated as 73% of the fat-free mass). Urine samples are obtained 4 and 5 hours after the dosing. On the mornings of days 7 and 14, subjects are instructed to discard their first urine void and collect the second urine void of the day. The aliquots are then analyzed in triplicate on the Triple Isotope Water Analyzer. Background fluctuations of $^2H$ and $^{18}O$ are calculated using the measured change in $^{17}O$. Turnover rates and the extrapolated dilution spaces at the time of dosing are calculated from the slope and intercept of the semi-log plot of urine isotope enrichment relative to the time after dosing. $CO_2$ production rate is calculated using a modification [J. Speakman, K. Nair, M. Goran, "Revised equations for calculating CO2 production from doubly labeled water in humans", American Journal of Physiology, 264 (1993) E912-917] of the original equation of Schoeller et al. [D. Schoeller, E. Ravussin, Y. Schutz, K. Acheson, P. Baertschi, E. Jequier, "Energy expenditure by doubly labeled water: validation in humans and proposed calculation", American Journal of Physiology, 250 (1986) R823-830]. $O_2$ consumption rate is calculated by dividing the $CO_2$ production rate assuming an RQ of 0.82. Total EE is then calculated using the equation of Weir [J. Weir, "New methods for calculating metabolic rate with special reference to protein metabolism", Nutrition, 6 (1990) 213-221]. TEE (kcal/d) is determined as the average daily EE over the 14 days of measurement. Using the $^{17}O$ to calculate background fluctuations will provide an estimated five-fold decrease in the uncertainty of the TEE calculations due to background fluctuation.

Example Testing Protocol with Reduced $^{18}O$ Dose

TEE is measured for a 14 day period using DLW. Upon subject arrival for the study, body weight is measured to ±0.1 kg and a baseline urine sample is obtained for determination of background enrichments of $^2H$, $^{18}O$ and $^{17}O$. Subjects are then given an oral dose of 0.05 g $H_2^{18}O$ and 0.12 g $^2H_2O$ per kg of total body water (estimated as 73% of the fat-free mass). Urine samples are obtained 4 and 5 hours after the dosing. On the mornings of days 7 and 14, subjects are instructed to discard their first urine void and collect the second urine void of the day. The aliquots are then analyzed in triplicate on the Triple Isotope Water Analyzer. Background fluctuations of $^2H$ and $^{18}O$ are calculated using the measured change in $^{17}O$. Turnover rates and the extrapolated dilution spaces at the time of dosing are calculated from the slope and intercept of the semi-log plot of urine isotope enrichment relative to the time after dosing. $CO_2$ production rate is calculated using a modification [J. Speakman et al., op. cit.] of the original equation of Schoeller et al. [op. cit.]. $O_2$ consumption rate is calculated by dividing the $CO_2$ production rate assuming an RQ of 0.82. Total EE is then calculated using the equation of Weir [op. cit.]. TEE (kcal/d) is determined as the average daily EE over the 14 days of measurement. Using the $^{17}O$ to calculate background fluctuations in this case reduces the cost of the measurement approximately 5-fold while, we estimate, maintaining current levels of uncertainty in TEE calculations.

Sample Analysis Example

The preferred instrument is an optical spectrometer capable of simultaneously measuring $\delta^2H$, $\delta^{18}O$, and $\delta^{17}O$. Samples collected from any doubly labeled water experiment can be analyzed using the instrument. The recommended protocol is as follows. Prepare the samples for analysis by the instrument. For urine samples, this involves centrifuging the samples and removing the supernatant for analysis, or samples can be carefully distilled. Preparation steps vary depending on the body water that is to be measured. Samples are pipetted into autosampler vials and loaded into an autosampler for automated analysis, or can be manually injected into the instrument. Calibration standards are measured throughout the analysis, interleaved between samples to continuously calibrate the instrument. The specific number of injections and frequency of calibration is dependent on the salinity and isotopic enrichment of the samples being analyzed. After analysis, the calibration standards are used to adjust the raw output of the instrument to give final measured values for $\delta^2H$, $\delta^{18}O$, and $\delta^{17}O$.

The invention claimed is:

1. A method of measuring energy expenditure in a living subject, comprising:
    administering a specified dose of doubly-labeled water ($^2H_2^{18}O$) to a living subject;
    obtaining samples at three or more times of body water from the living subject;
    measuring $^2H/^1H$, $^{17}O/^{16}O$ and $^{18}O/^{16}O$ ratios in each of the obtained samples using optical spectroscopy; and
    determining (1) a combined value of flux of body water and exhaled carbon dioxide from a change in measured $^{18}O/^{16}O$ over time, (2) a value of flux of body water alone from a change in measured $^2H/^1H$ over time, and (3) a reference value of isotopic background fluctuation from a change in measured $^{17}O/^{16}O$ over time, wherein the specified dose is selected to be a low-enrichment dose that produces an initial $\delta(^{18}O)$ enrichment in the body water of the subject of +20‰ relative to VSMOW.

2. A method of measuring energy expenditure in a living subject, comprising:
    administering a specified dose of doubly-labeled water ($^2H_2^{18}O$) to a living subject;
    obtaining samples at three or more times of body water from the living subject;
    measuring $^2H/^1H$, $^{17}O/^{16}O$ and $^{18}O/^{16}O$ ratios in each of the obtained samples using optical spectroscopy; and
    determining (1) a combined value of flux of body water and exhaled carbon dioxide from a change in measured $^{18}O/^{16}O$ over time, (2) a value of flux of body water alone from a change in measured $^2H/^1H$ over time, and (3) a reference value of isotopic background fluctuation from a change in measured $^{17}O/^{16}O$ over time, wherein the specified dose is selected to be a precision-measurement dose that produces an initial $\delta(^{18}O)$ enrichment in the body water of the subject of at least +100‰ relative to VSMOW.

3. A method of measuring energy expenditure in a living subject, comprising:
    administering a specified dose of doubly-labeled water ($^2H_2^{18}O$) to a living subject;
    obtaining samples at three or more times of body water from the living subject;
    measuring $^2H/^1H$, $^{17}O/^{16}O$ and $^{18}O/^{16}O$ ratios in each of the obtained samples using optical spectroscopy; and
    determining (1) a combined value of flux of body water and exhaled carbon dioxide from a change in measured $^{18}O/^{16}O$ over time, (2) a value of flux of body water alone from a change in measured $^2H/^1H$ over time, and (3) a reference value of isotopic background fluctuation from a change in measured $^{17}O/^{16}O$ over time, wherein measured change in $^{18}O/^{16}O$ is adjusted by the measured change in $^{17}O/^{16}O$.

4. The method as in claim 3, wherein the optical spectroscopy comprises off-axis integrated cavity output spectroscopy.

5. The method as in claim 3, wherein the dose of doubly-labeled water is administered by oral ingestion.

6. The method as in claim 3, wherein the dose of doubly-labeled water is administered by injection.

7. The method as in claim 3, wherein samples of the bodily water are obtained by collection of any of urine, blood, plasma, saliva, and breath from the subject.

8. The method as in claim 3, wherein samples are obtained at regular intervals over a period of at least two weeks.

9. The method as in claim 8, wherein samples are obtained initially 4 to 5 hours after dosing, then on days 7 and 14 after dosing.

* * * * *